(12) United States Patent
Fischer et al.

(10) Patent No.: US 10,435,338 B2
(45) Date of Patent: Oct. 8, 2019

(54) METHOD AND PROCESS FOR CONVERTING THE ETHYLENE PRESENT IN THE OVERHEAD EFFLUENT FROM A FCC IN A MANNER SUCH AS TO INCREASE THE PROPYLENE PRODUCTION

(71) Applicant: IFP Energies nouvelles, Rueil-Malmaison (FR)

(72) Inventors: Beatrice Fischer, Lyons (FR); Vincent Coupard, Villeurbanne (FR)

(73) Assignee: IFP Energies nouvelles, Rueil-Malmaison (FR)

(*) Notice: Subject to any disclaimer, the term of this patent is extended or adjusted under 35 U.S.C. 154(b) by 0 days.

(21) Appl. No.: 16/034,572

(22) Filed: Jul. 13, 2018

(65) Prior Publication Data

US 2019/0016648 A1  Jan. 17, 2019

(30) Foreign Application Priority Data

Jul. 13, 2017 (FR) ...................... 17 56712

(51) Int. Cl.

| | |
|---|---|
| *C07C 2/76* | (2006.01) |
| *C07C 7/11* | (2006.01) |
| *C07C 7/00* | (2006.01) |
| *F25J 3/02* | (2006.01) |
| *B01D 53/04* | (2006.01) |
| *C10G 50/00* | (2006.01) |
| *C10G 53/04* | (2006.01) |
| *C10G 53/06* | (2006.01) |
| *C10G 55/06* | (2006.01) |

(Continued)

(52) U.S. Cl.
CPC ............ *C07C 2/76* (2013.01); *B01D 53/0423* (2013.01); *C07C 7/005* (2013.01); *C07C 7/11* (2013.01); *C10G 11/18* (2013.01); *C10G 21/00* (2013.01); *C10G 50/00* (2013.01); *C10G 53/04* (2013.01); *C10G 53/06* (2013.01); *C10G 55/06* (2013.01); *C10G 57/02* (2013.01); *C10G 70/048* (2013.01); *C10G 70/06* (2013.01); *F25J 3/0209* (2013.01); *F25J 3/0242* (2013.01); *F25J 3/0247* (2013.01); *C10G 2400/02* (2013.01); *C10G 2400/20* (2013.01); *C10G 2400/30* (2013.01); *F25J 2215/64* (2013.01); *F25J 2215/66* (2013.01)

(58) Field of Classification Search
CPC .................................. C10G 55/06; C07C 7/11
USPC .............................................. 208/67, 71, 113
See application file for complete search history.

(56) References Cited

U.S. PATENT DOCUMENTS 4,091,046 A * 5/1978 Dixon ...................... C07C 11/18
585/315
4,831,203 A * 5/1989 Owen ...................... C10G 57/02
585/519

(Continued)

OTHER PUBLICATIONS

Wang Y. et. al. "Catalytic Conversion of Ethylene to Propylene and Butenes over H-ZSM-5", Ind. Eng. Chem. Res., (2009), 48, pp. 10788-10795. (Year: 2009).*

(Continued)

*Primary Examiner* — Philip Y Louie
(74) *Attorney, Agent, or Firm* — Millen White Zelano & Branigan, PC

(57) ABSTRACT

A gaseous fraction leaving overhead from a fractionation column of a catalytic cracking unit (FCC) is fractionated using a unit for the conversion of ethylene into propylene, in order to upgrade the ethylene contained in the fuel gas.

8 Claims, 5 Drawing Sheets

(51) Int. Cl.
*C10G 57/02* (2006.01)
*C10G 70/04* (2006.01)
*C10G 70/06* (2006.01)
*C10G 11/18* (2006.01)
*C10G 21/00* (2006.01)

(56) References Cited

U.S. PATENT DOCUMENTS

| | | | |
|---|---|---|---|
| 5,034,565 A * | 7/1991 | Harandi | C10G 50/00 585/415 |
| 2007/0185359 A1 | 8/2007 | Umansky | |
| 2011/0243797 A1* | 10/2011 | da Silva Ferreira Alves | C10G 11/18 422/134 |

OTHER PUBLICATIONS

Epelde, E. et. al. "Modifications in the HZSM-5 zeolite for the selective transformation of ethylene into propylene", Applied Catalysis A: General, (2014), 479, pp. 17-25. (Year: 2014).*
Hong, S. B. et. al. "MSE-Type Zeolites: A promising Catalyst for the Conversion of Ethene to Propene", ACS Catalysis, (2016), 6, pp. 3870-3874. (Year: 2016).*
Ernst, S. et. al. "Influence of the pore architecture on the selective conversion of ethene to propene and butenes over medium pore zeolites", New J. Chem., (2016), 40, pp. 4414-4419. (Year: 2016).*
French Search Report 1756712 dated Mar. 15, 2018.

* cited by examiner

METHOD AND PROCESS FOR CONVERTING THE ETHYLENE PRESENT IN THE OVERHEAD EFFLUENT FROM A FCC IN A MANNER SUCH AS TO INCREASE THE PROPYLENE PRODUCTION

CONTEXT OF THE INVENTION

In a catalytic cracking unit (generally known as FCC), at the outlet from the reaction/regeneration assembly, there is a fractionation column which can be used to separate the heavy fractions, the heavy naphtha and the light fractions: gas, LPG and light gasoline which is found at the head of the column. These light overhead fractions are then sent to a section in order to recover a maximum amount of LPG and gasoline, and to optionally purify the gas before sending it as fuel gas. This gas, known as "fuel gas", contains a non-negligible quantity of ethylene (sometimes denoted C2--), which is often burned with the fuel gas. A fairly complete reference can be found in: "The Fluid Catalytic Cracking Handbook"—Reza Sadeghbeigi—3rd edition—Chapter 1.

In rare cases, the fuel gas is purified further by means of a cryogenic fractionation in order to recover the ethylene. This option is expensive and is only justified for large units with large flow rates of ethylene. The compounds which in practice are the most sought-after are the propylene (sometimes denoted C3--), and the gasoline, and many patents exist which attempt to increase their production. There is a current tendency aimed at increasing the FCC yield for propylene: the normal yield is less than 5%, but by changing the type of feed and the operating conditions, up to 18% of propylene with respect to the feed can be obtained. The quantity of ethylene produced is also increased, but since the ethylene leaves in the gaseous form, highly diluted with nitrogen, carbon dioxide, hydrogen, methane, ethane, other alkanes, other olefins and other impurities (CO, $H_2S$, $NH_3$, $SO_2$, $NO_2$, etc.), it is very difficult to recover and is generally sent to the refinery as fuel gas.

BRIEF DESCRIPTION OF THE INVENTION

Figure 1:
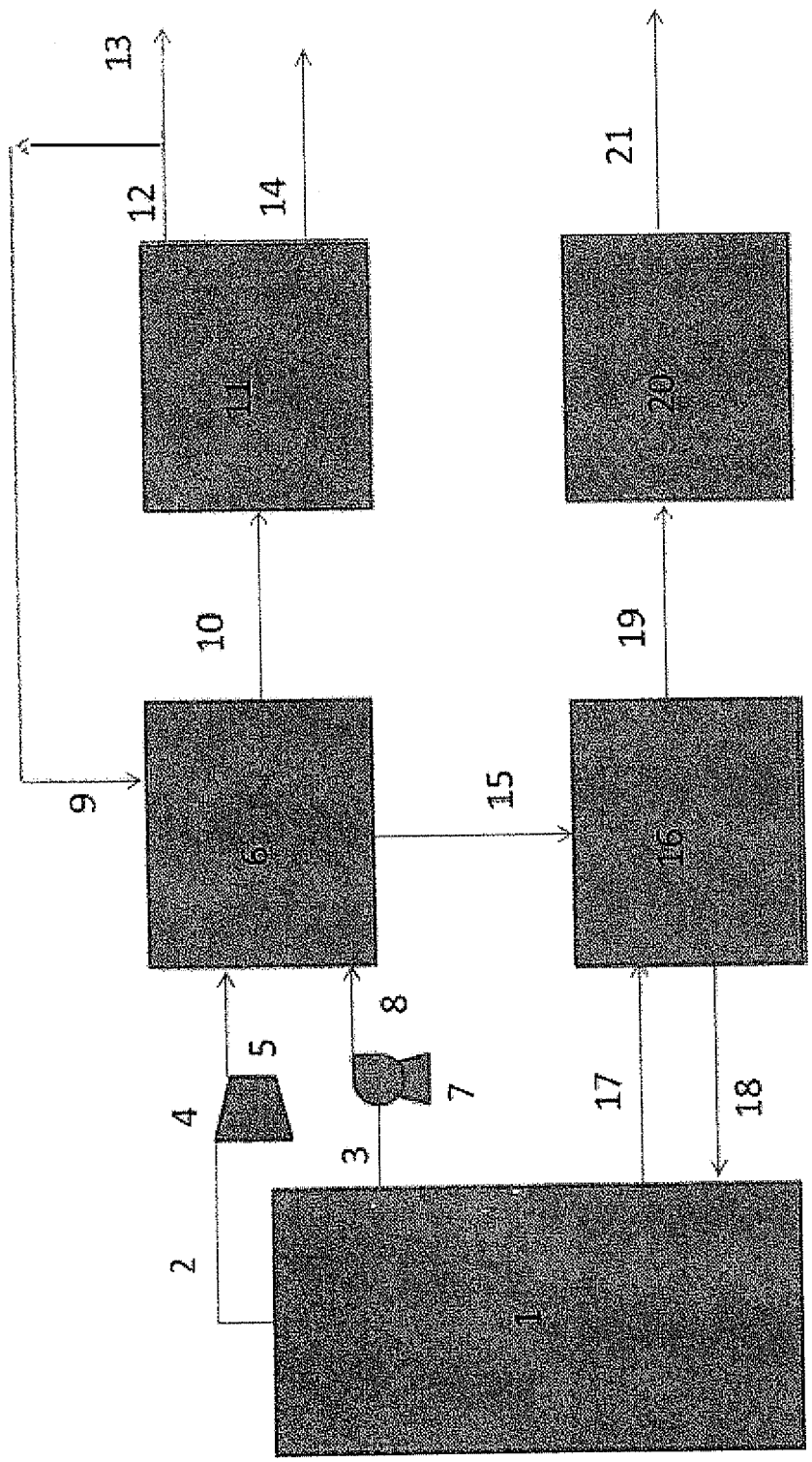
FIG. 1, which is in accordance with the prior art, represents the process flow diagram for fractionation of the effluents from a catalytic cracking unit (FCC) limited to the light portion of said effluents, i.e. to the light gasoline, to the LPG and to a residual gas termed the "fuel gas" because, in accordance with the prior art, this gas is usually sent to the fuel system of the refinery without subsequent separation.

The present invention consists of a process for transforming the ethylene contained in the fuel gas, i.e. the overhead gas obtained from fractionation of the effluents from a catalytic cracking unit, after separation of the light gasoline fraction and LPG, into propylene and other recoverable products. The overhead gas obtained from fractionation of the effluents from a FCC unit in fact contain a light gasoline fraction, LPG (liquefied petroleum gas) and a residual gas which is generally used as a fuel. However, this fuel gas contains a certain proportion of ethylene which it is possible to upgrade, by means of a reaction for transforming the ethylene principally into propylene and other products of interest, which requires a catalytic conversion unit which is incorporated into the process flow diagram for the treatment of the overhead effluents of the prior art.

The aim of the present invention is thus to recover the major proportion of the ethylene contained in the fuel gas, in order to convert it principally into propylene. Other upgradable products, essentially butene and aromatics, are also produced. These products will be respectively recovered in the LPG and in the gasoline cut.

The unit for the conversion of ethylene into propylene is integrated into the process flow diagram for fractionation of the overhead effluents from the FCC, which, more precisely, is known as the recovery section for the treatment of the light effluents leaving the principal fractionation overhead.

The catalyst used in the unit for the conversion of ethylene into propylene comprises a zeolite (e.g. aluminosilicate microporous crystal) which, at high temperature (in the range 500° C. to 650° C.), means that it can be operated without being deactivated too rapidly, despite the non-hydrocarbon impurities present with the ethylene of the feed. The preferred catalyst is a catalyst comprising ZSM-5 in an inert matrix, for example silica. Post-treatments may be carried out on this catalyst in order to limit its deactivation cycle. Any zeolite which can be used to carry out olefin interconversion reactions (i.e. conversion between olefins, as carried out by the conversion unit 22) can be adapted to this process. The conversion of ethylene into propylene is highly exothermic, but because the ethylene is very diluted, and because other reactions pertaining to other olefins present in the mixture are endothermic, this high exothermicity is not a problem, and in many cases it is possible to use a single reactor. In general, the exothermicity of the reaction for conversion of C2-- to C3-- is used to preheat the feed by means of a feed-effluent exchanger.

The reactor or reactors used for the C2-- to C3-- conversion reaction are upflow or downflow or radial reactors, i.e. with a transverse flow of feed through the catalytic bed. The catalytic bed may be of the fixed bed or moving bed type. A moving bed is a gravity flow bed of the type found in units for the catalytic reforming of gasolines.

The reactor or reactors are also coupled with a combustion regeneration loop, allowing the process to be operated continuously. The conversion reaction necessitates a partial pressure of olefins in the range 1 to 2 bars (and preferably between 1.25 and 1.75 bar), but because of the high dilution, operation at a pressure in the range 6 to 12 bar is possible depending on the case, i.e. a pressure which is not too far from the pressure of the recovery section (15-20 bar).

The regeneration is carried out at the same temperature as the reaction operation and preferably at the same pressure, which means that a reactor can be moved rapidly from reaction mode to regeneration mode, and from regeneration mode to reaction mode. The reactor swung into regeneration mode (while the regenerated reactor is swung into reaction mode) is connected to a regeneration section comprising a feed/effluent exchanger, a cooling exchanger, a separator allowing the water of reaction to condense, and a compressor for recirculating the regeneration gas.

Regeneration may be carried out by burning coke deposited on the catalyst over a few hours, by injecting a suitable quantity of air into the regeneration gas, optionally diluted with an inert gas, for example nitrogen or oxygen-depleted combustion gases, in order to produce an increase in temperature in the reactor which is limited to a maximum of 50° C., which means that a regeneration furnace can be dispensed with. The number of reactors is adapted so that at all times, at least one reactor is in reaction mode and one reactor is in regeneration mode.

The positioning of the conversion unit between the first and second absorption section which generally already exist in a fractionation process flow diagram in accordance with the prior art, means that a FCC can be remodelled easily and at low cost, without changing the existing main equipment. The supplemental production of propylene is of the order of 10%, which means that the downstream units (the column termed "superfractionation", in particular propane-propylene) can absorb this supplemental production with minor modifications, or even without any modification if the dimensioning margins are sufficient.

More precisely, the present invention consists of a process for fractionating the gaseous fraction leaving a fractionation column of a catalytic cracking unit (FCC) overhead, the fraction containing LPG (abbreviation for liquefied petroleum gas), light gasoline, and a residual gas termed "fuel gas" which itself contains a certain quantity of ethylene. It is this ethylene which the present invention is seeking to upgrade into propylene and other products of interest.

The process in accordance with the invention generally comprises:
  a first absorption section 6 which can be used to separate the fuel gas 15 and the light gasoline and LPG stream 10, this section generally existing in a FCC, and not necessitating any modification as a result of installing equipment in accordance with the present invention (conversion unit 22, and sections for absorption 31 and debutanization 35),
  a unit 22 for the conversion of ethylene into propylene, in which a large proportion of the ethylene is essentially converted into propylene, into aromatics and other products of interest, the other olefins present (C4, C5+) also being partially converted, essentially into propylene,
  a novel absorption section 31, which admits the effluents from the conversion unit 22 after separation in the separator 24, producing a gas phase 25 which is recompressed in the compressor 26 before entering the novel absorption section 31, and a liquid phase 28 which is pumped by means of the pump 29 in order to enter the novel absorption section 31 as well. The propylene, the butene, the gasoline fractions contained in the gas fraction 27 and the liquid fraction 30 are recovered in said absorption section 31, by using the gasoline 32 arriving from the existing debutanizer 11,
  a second absorption section 16, which admits the gas 33 obtained from the novel absorption section. This second absorption section 16 generally exists in a conventional FCC process flow diagram, and does not need any modification which could be involved when installing the equipment in accordance with the present invention (i.e. the absorption section 31 described above, and the conversion unit 22, and the debutanization section 35 described below),
  a novel debutanization section 35 which admits the LPG and gasoline fractions 34 obtained from the novel absorption section 31 and which produces a stabilized gasoline 36 and a light fraction 37 which can be mixed with the LPG produced.

The unit 22 for the conversion of ethylene into propylene and other products of interest is a catalytic unit using a catalyst based on zeolite operating at a temperature in the range 500° C. to 650° C. and at a partial pressure of olefins in the range 1 to 2 bars.

In accordance with a first variation of the fractionation process in accordance with the present invention, a portion of the gas stream 27 obtained from the unit for the conversion of ethylene into propylene and other products of interest 23 is recycled to the inlet to the conversion unit after compression in the compressor 26, said recycled fraction possibly being varied between 10% and 75% of the total stream 27 arriving in the section 31.

In the fractionation process in accordance with the present invention, the unit 22 for the conversion of ethylene into propylene and other products of interest comprises at least two reactors 223 and 227 separated by an intermediate cooling of the effluent 224 from the first reactor 223 going towards the second reactor 227, by means of a first exchanger 225, then at the outlet from the reactor 227, the converted effluent 228 is sent to the feed-effluent exchanger 221, where it is cooled by indirect exchange with the feed 15, then towards the chiller 230, where the cooling is terminated with the aid of cooling water.

In accordance with another variation of the fractionation process in accordance with the present invention, the feed 15 for the conversion unit 22 arrives at the feed-effluent exchanger 221 as a mixture with the recycled stream 38 obtained from a portion of the stream 27, where the two mixed streams are preheated to the operating temperature, then sent to the reactor 223 of the conversion unit 22, the converted effluent 228 being sent to the feed-effluent exchanger 221, in which it is cooled by indirect exchange with the feed 15, then towards the chiller 230 in which cooling is terminated with the aid of cooling water, the cooled effluent 23 being sent to a separator 24, in which the liquid phase is separated from the gas phase, said gas phase 25 being compressed by the compressor 26 then sent to the absorption section 31, and the liquid 28 being sent to the absorption section 31 via the pump 29.

In accordance with a preferred variation of the fractionation process in accordance with the present invention, the unit 22 for the conversion of ethylene into propylene and other products of interest functions with a zeolite-based catalyst under the following operating conditions:
  temperature in the range 500° C. to 650° C.,
  partial pressure of ethylene in the range 1 to 2 bar absolute.

DETAILED DESCRIPTION OF THE INVENTION

The present invention will be better understood from the description of the figures which illustrate it. FIG. 1 is in accordance with the prior art, and FIGS. 2, 3, 4 and 5 are in accordance with the present invention.

Description of FIG. 1 (in Accordance with the Prior Art):

fractionation of light fractions leaving the FCC. A vapour distillate 2 and a liquid distillate 3 leave the principal FCC fractionation column 1 overhead. These two fractions essentially comprise light hydrocarbons (paraffins and olefins), from methane to light gasoline, hydrogen, nitrogen, oxides of carbon (CO and $CO_2$), water, and small quantities of $H_2S$ and $NH_3$, as well as traces of SOx and NOx. The vapour fraction is compressed by the compressor 4 and sent to a first absorption section 6 via the conduit 5.

The liquid fraction is pumped by the pump 7 and sent to the absorption section 6 via the conduit 8. This section uses an absorption gasoline arriving via the conduit 9 to recover the essential part of the liquid fractions, which are sent via the conduit 10 to a debutanization section 11 where the gasoline leaving via the conduit 12 is separated from the LPG (C3/C4) leaving via the conduit 14. A portion of the gasoline is returned to the section 6 via the conduit 9, and the remainder constitutes the gasoline product, sent out of the unit via the conduit 13.

The gaseous fraction which has lost the essential portion of the LPG and gasoline also leaves the section 6 via the conduit 15. To finish recovery of the rest of the upgradable products, this gas is sent to a second absorption section 16 where a heavy cut arriving from the fractionation column 1 via the conduit 17 can be used to return a large portion of this remaining LPG and gasoline to the column via the conduit 18 with the heavy cut. The purified light gas is sent to a purification section 20 via the conduit 19 before being sent as fuel gas via the conduit 21.

All of the ethylene contained in the stream 21 is burned. Recovering it would necessitate very intense purification followed by cryogenic distillation, which would involve investment which would frequently be considered to be too high having regard to the quantity produced. The aim of the present invention is to transform the ethylene without purifying it and essentially to convert it into propylene and other products of interest which will be recovered in part in the existing unit. This will be better understood in the light of FIG. 2, which represents a process flow diagram of the process in accordance with the invention.

Figure 2:
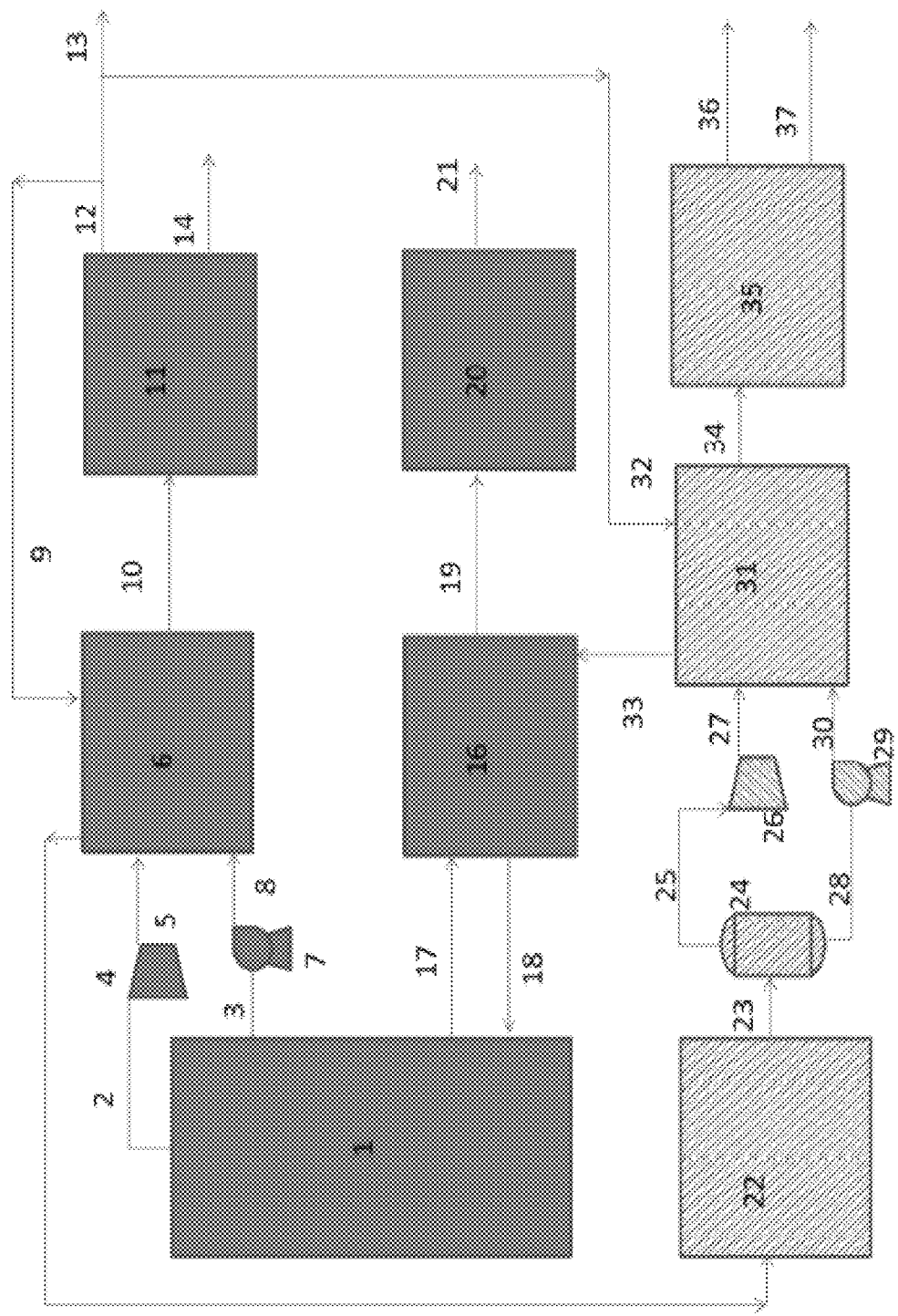
FIG. 2 represents the basic process flow diagram for the process in accordance with the invention, in which the fuel gas is sent to a unit 22 for the conversion of ethylene into propylene. The process flow diagram is supplemented by an absorption section 31 and a debutanization section 35.

Description of FIG. 2 (in Accordance with the Invention):

fractionation of light fractions leaving the FCC, with conversion of ethylene into propylene and other products of interest.

The gaseous fraction leaving the section 6 via the conduit 15 is no longer sent to the second absorption section 16, but to the novel conversion unit 22, in which a large proportion of the ethylene is essentially converted into propylene, into aromatics, and into other products of interest. The other olefins present (C4, C5+) are also partially converted, essentially into propylene. At the outlet from the unit 22, the gas is at a lower pressure, and has to be recompressed in order to be sent to an absorption section. It is thus sent via the conduit 23 to a separator 24, the vapour phase being sent via the conduit 25 to a compression device 26 from which it leaves via the conduit 27 at a higher pressure.

The liquid phase is sent via the conduit 28 to the pump 29, from which it leaves via the conduit 30 at a higher pressure and enters the absorption section 31. The propylene, butene and the gasoline fractions contained in the gas 25 are recovered in the absorption section 31 by using gasoline arriving via the conduit 32 from the existing debutanizer 11. After absorption, the gas is sent via the conduit 33 to the existing secondary absorption section 16 and the LPG and gasoline fractions are sent to the debutanization section 35 via the conduit 34. The stabilized gasoline leaves via the conduit 36 and can be sent to store as a mixture with the gasoline leaving via the conduit 13. The light fraction from the debutanizer leaves via the conduit 37 and can be mixed with the LPG produced, which leaves via the conduit 14.

It would be possible to use the existing sections 6 and 11 instead of using the novel equipment corresponding to the novel sections 31 and 35. However, the equipment of sections 6 and 11 would run the risk of being insufficient and would necessitate major modifications, which would mean that the FCC unit would have to be stopped for several months. The advantage of creating the novel sections 31 and 35 is that they enable an existing FCC to be revamped without major modifications, solely with a few connections to the novel unit, which could be carried out in a short time period during a normal stoppage.

Figure 3:
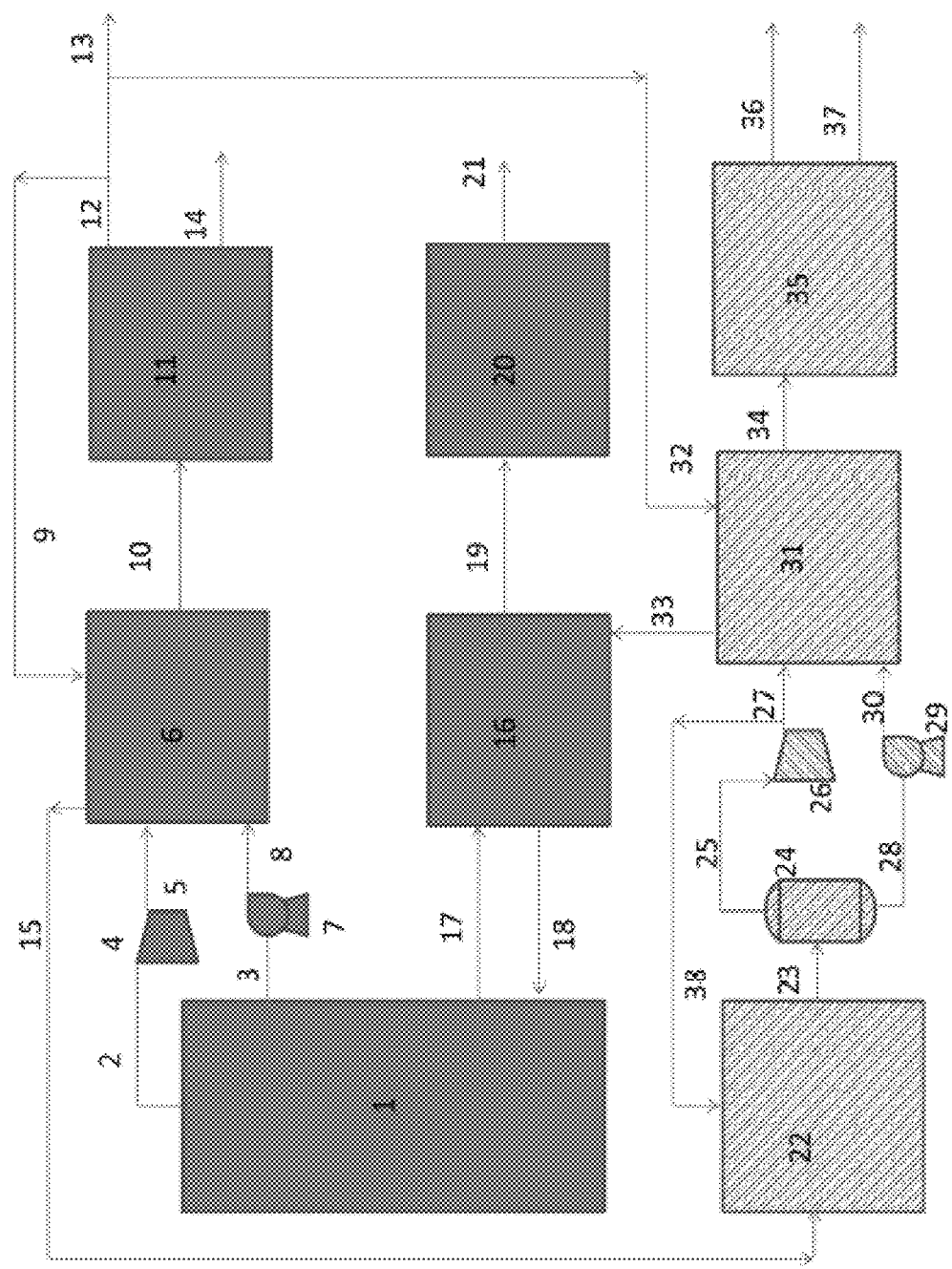
FIG. 3 represents a variation in the process flow diagram in accordance with the invention, in which the conversion of ethylene in the conversion unit 22 is not complete; it may be advantageous to recycle a portion of the gas leaving the conversion unit 22, after compression in the compressor 26, to the conversion section 22 by means of a conduit 38.

Description of FIG. 3 (Variation in Accordance with the Invention):

fractionation of light fractions leaving the FCC with conversion of the ethylene into propylene and other products of interest, and recycling a portion of the gas leaving the conversion unit.

The conversion of ethylene in the conversion unit 22 is not complete, and so it might be advantageous to recycle a portion of the gas leaving the conversion unit 22, compressed by the compressor 26, to the conversion section 22 via the conduit 38.

After conversion, the ethylene is still more diluted than in the feed 15, which means that the pressure in the conversion reactor can be higher for the same partial pressure of olefins, which is economically favourable. In addition, the exothermicity of the propylene conversion reaction is reduced, which means that a single reactor can be used, and thus the cost of the unit can be reduced, despite its increased capacity.

Figure 4:
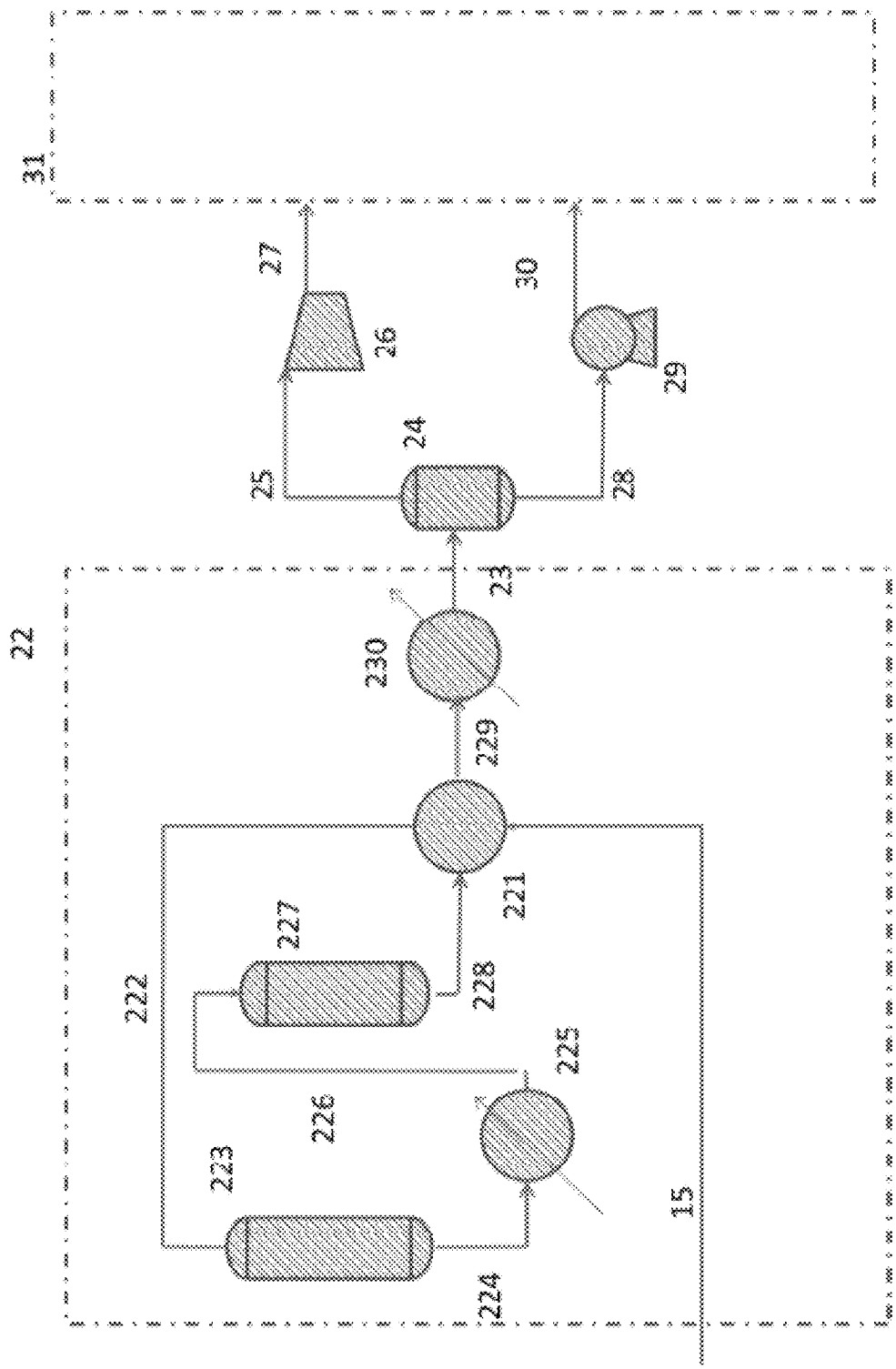
FIG. 4 shows, in more detail, the unit 22 for the conversion of ethylene into propylene in accordance with the invention. The principal reaction is highly exothermic, and so it is necessary to have at least two reactors 223 and 227 with intermediate cooling, 225.

Description of FIG. 4 (Conversion Section in Accordance with the Invention):

ethylene conversion unit with two reactors with intermediate cooling.

The stream leaving the existing absorber 6 arrives via the conduit 15 in the feed-effluent exchanger 221 where it is preheated to the operating temperature and sent to the first reactor 223 via the conduit 222. Because the reaction is highly exothermic, it is necessary to cool at the outlet from this first reactor by generating vapour 225 in order to cool the effluent 224 to the operating temperature. The cooled stream is sent to the second reactor 227 via the conduit 226. Two reactors 223 and 227 are shown in this process flow diagram. In certain cases, it could be necessary to install more if the proportion of ethylene at the inlet, and thus the exothermicity of the reaction for the conversion of ethylene into propylene, is very high. At the outlet from the second reactor 227, the converted effluent is sent via the conduit 228 to the feed-effluent exchanger 221, where it is cooled by indirect exchange with the feed, and then is sent via the conduit 229 to the chiller 230, in which cooling is terminated with the aid of cooling water. It is also possible to use air to provide the cooling in the chiller 230.

At the outlet from the chiller 230 of this exchanger, the effluent is sent via the conduit 23 to a separator 24, where the liquid phase is separated from the gas phase. The gas phase is taken into the conduit 25, compressed by the compressor 26, and sent to an absorption section via the conduit 27. The liquid withdrawn via the conduit 28 is sent to the same absorption section via the pump 29 and the conduit 30.

This first variation generally necessitates a number of 2, 3 or 4 reactors 223 operating in series, plus a certain number operating in regeneration mode in order to provide for continuous operation, plus optionally again a certain number "in reserve", in case the service life of the catalyst is less than 1 year, in order to be able to change the catalyst while continuing to operate. In addition, the pressure drops in all of these reactors, to which the pressure drop in the vapour generator or generators has to be added, increase the compression ratio in the gas take-up compressor, and thus its cost and its consumption of electricity. Finally, the CAPEX and OPEX are fairly high.

For this reason, it is possible to recycle a portion of the gaseous effluent obtained from the separator 24 in order to further dilute the olefins, reduce the exothermicity and increase the operating pressure, which reduces the cost and consumption of the compressor 26. The other equipment is thus more expensive, because their capacities and operating pressures are higher, but the number of reactors 223 is reduced. It is possible to operate with a single reactor with a sufficient recycle ratio, i.e. a total of 3 reactors: 1 in operational mode, 1 in regeneration mode and 1 "in reserve".

Figure 5:
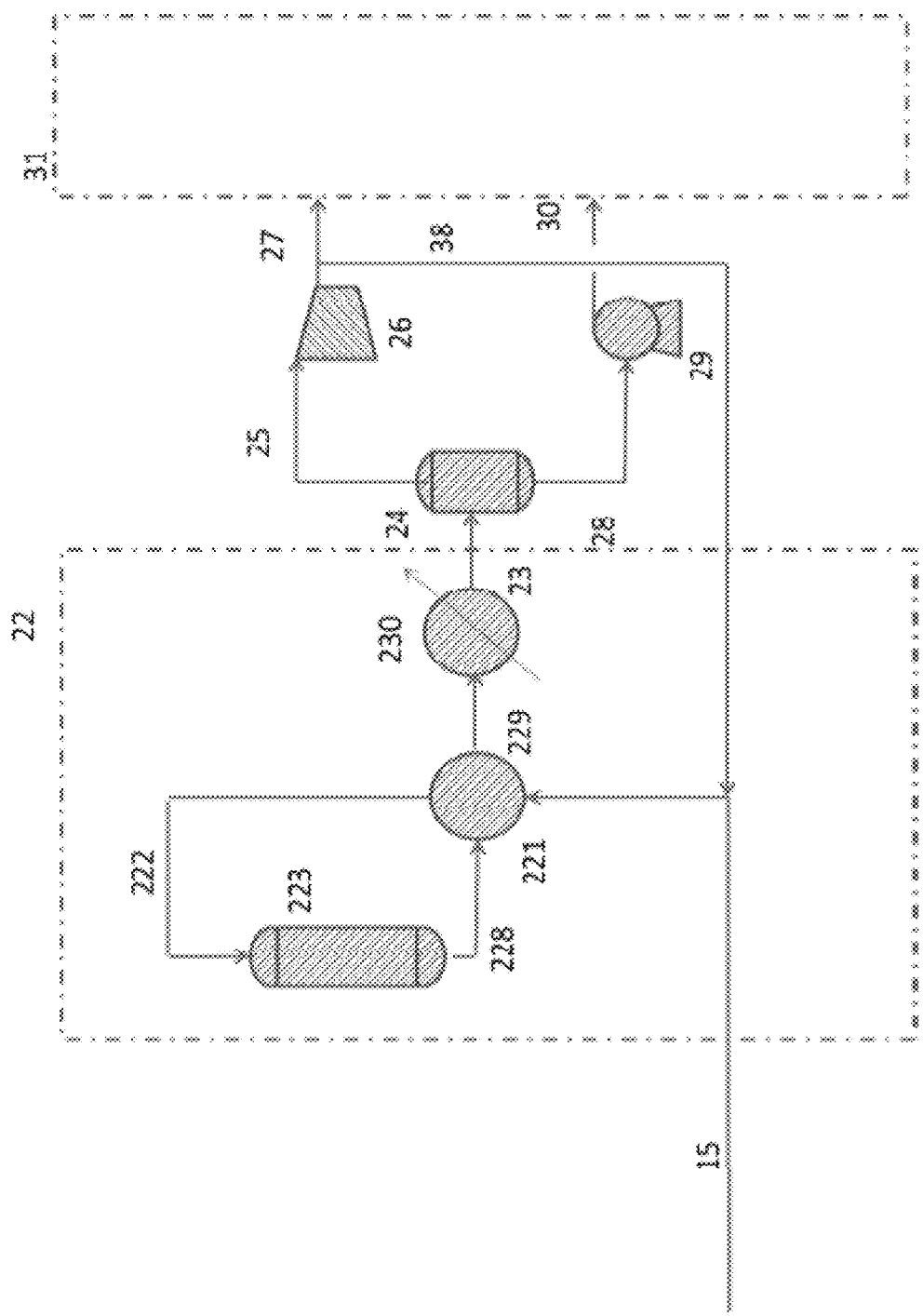
FIG. 5 shows a variation in the conversion unit 22 in accordance with the invention, in which the feed for the unit 22 for the conversion of ethylene into propylene comprises a high proportion of recycled effluent 222, which means that the unit can function with a single reactor 223.

The start-up equipment (in particular the start-up furnace) and regeneration equipment (compressor, exchangers, separator, etc) are not shown in FIGS. 4 and 5.

Description of FIG. 5 (Variation of the Conversion Section in Accordance with the Invention):

unit for the conversion of ethylene into propylene and other products of interest in a single reactor, and recycle of a portion of the effluent from the conversion unit.

The stream leaving the existing absorber 6 arrives at the feed-effluent exchanger 221 via the conduit 15 as a mixture with the recycle arriving via the conduit 38, where it is preheated to the operating temperature and sent to the reactor 223 via the conduit 222. The reaction is highly exothermic, but with the dilution due to recycling, it is possible to have a moderate increase in temperature of approximately 30° C. to 50° C., and thus to operate with a single reactor. At the outlet from the reactor 223, the converted effluent is sent via the conduit 228 to the feed-effluent exchanger 221, where it is cooled by indirect exchange with the feed, and then is sent via the conduit 229 to the chiller 230, where cooling is terminated with the aid of cooling water. It is also possible to use air for cooling. At the outlet from this exchanger, the effluent is sent via the conduit 23 to a separator 24, where the liquid phase is separated from the gas phase. The gas phase is taken up into the conduit 25, compressed by the compressor 26 and sent to the absorption section 31.

The liquid withdrawn via the conduit 28 is sent to the absorption section 31 via the pump 29 and the conduit 30.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 17/56.712, filed Jul. 13, 2018 are incorporated by reference herein.

EXAMPLES IN ACCORDANCE WITH THE INVENTION

Example 1

In this first example which is in accordance with the invention, a FCC unit was considered which had a capacity of 2 MT/year, operating in order to produce a maximum quantity of propylene (C3--).

The process was operated in accordance with the process flow diagrams of FIGS. 2 and 4. The unit 22 for the conversion of ethylene into propylene was operated using two reactors, one in reaction mode while the other was in regeneration mode.

The feed arriving at the ethylene conversion unit via the conduit 15 had a flow rate of 16350 kg/h, with the following composition (as a mole %):

Nitrogen: 17.8
Hydrogen: 14.2
Methane: 27.3
Ethane: 13.7
Ethylene: 13.7
Propane: 0.3
Propylene: 3.2
Butane: 0.3
Butenes: 0.4
Gasoline: 3.9
Water: 0.5
CO: 1.0
$CO_2$: 3.8
$H_2S$, $NH_3$, SOx, NOx were in trace amounts The pressure at the inlet to the conversion reactors was 7.8 bar absolute, which meant that the partial pressure of olefins was 1.5 bar, and the pressure at the inlet to the compressor was 5.5 bar.

The inlet temperature of the reactors was 550° C. Two reactors were operated in series, with an increase in the temperature at the reactor outlet of 43° C. in each reactor, and intermediate cooling by generating vapour. 390 kg/h of liquid was present in the separator.

At the outlet from the second reactor, the composition was as follows (as a mole %):

Nitrogen: 18.7
Hydrogen: 15.0
Methane: 28.7
Ethane: 14.4
Ethylene: 2.9
Propane: 0.7
Propylene: 8.5
Butane: 0.7
Butenes: 0.6
Gasoline: 4.5
Water: 0.5
CO: 1.0
CO2: 3.8
$H_2S$, $NH_3$, SOx, NOx were in trace amounts Overall, the propylene production, which was 21 tonnes/h without ethylene conversion, was increased by 1.8 tonne/h, i.e. by 9%, and also a small supplemental quantity of butenes (70 kg/h) and gasoline (400 kg/h) was produced.

Example 2

Consider a FCC unit with a capacity of 2 MT/year, operated to produce a maximum of propylene. The operation followed FIGS. 3 and 5, i.e. with a recycle of a portion of the gas leaving the conversion unit 22, after compression by the compressor 26, to the conversion section 22 by means of the conduit 38.

The feed arriving at the ethylene conversion section via the conduit 15 had a flow rate of 16350 kg/h, as in Example 1, with the same composition as in Example 1.

The recycle at the compressor outlet was 15150 kg/h. The pressure at the reactor inlet was 9 bar abs, which meant that the partial pressure of olefins was 1.5 bar, and the compressor inlet pressure was 7.7 bar. The temperature at the reactor inlet was 550° C.

A single reactor was used in the conversion unit 22 and the temperature increase in the reactor was 44° C. 660 kg/h of liquid was present in the separator 24.

At the outlet from the second reactor, the composition was as follows (as a mole %):
Nitrogen: 18.8
Hydrogen: 15.0
Methane: 28.9
Ethane: 14.6
Ethylene: 1.6
Propane: 0.7
Propylene: 10.2
Butane: 0.7
Butenes: 0.4
Gasoline: 3.5
Water: 0.5
CO: 1.0
CO2: 3.9
H2S, NH3, SOx, NOx were in trace amounts.

Overall, the propylene production, which was 21 tonnes/h without ethylene conversion, was increased by 2.3 tonnes because of the unit 22 for the conversion of ethylene into propylene, i.e. a gain of 11%. As an additional secondary effect of the invention, a small supplemental flow of butenes (30 kg/h) and gasoline (200 kg/h) was generated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for fractionating a gaseous fraction discharged from the head of a fractionation column of a catalytic cracking unit, the gaseous fraction containing liquefied petroleum gas (LPG), gasoline, and a residual gas termed "fuel gas" which itself contains a certain quantity of ethylene, comprising the following steps:
   separating the gaseous fraction into a fuel gas (15) and a liquid fraction containing gasoline and LPG (10) in a first absorption section (6),
   separating said liquid fraction (10) into gasoline and LPG in a first debutanizer section (11),
   introducing said fuel gas (15) into a catalytic conversion unit (22) containing a zeolite catalyst, wherein ethylene contained in said fuel gas (15) is converted into propylene and aromatics, in the presence of said zeolite catalyst,
   removing effluents from the catalytic conversion unit (22) and, after recompression, introducing said effluents into a first absorption section (31) wherein propylene, butene and gasoline fractions contained in said effluents are recovered in said first absorption section (31) by using an absorbent, wherein said absorbent is gasoline obtained from said first debutanization section (11),
   introducing a gas stream (33) obtained from said first absorption section (31) into a second absorption section (16), and
   introducing propylene, butene and gasoline fractions (34) recovered in said first absorption section (31) into a second debutanizer section (35) wherein a stabilized gasoline (36) and an LPG fraction (37) are produced.

2. The process as claimed in claim 1, wherein said catalytic conversion unit (22) comprises at least two reactors (223) and (227) separated by an intermediate heat exchanger (225) for cooling effluent (224) from the first reactor (223) before being introduced into the second reactor (227), and a chiller (228) for cooling converted effluent discharged from the second reactor (227).

3. The process as claimed in claim 1, wherein the effluents removed from the catalytic conversion unit (22) comprise a gas stream effluent (27), and a portion (38) of the gas stream effluent (27) is recycled to the catalytic conversion unit (22), after compression in a compressor (26).

4. The process as claimed in claim 1, wherein said catalytic conversion unit (22) comprises two reactors, wherein the two reactors of said catalytic conversion unit (22) function in alternation, one being in reaction mode and the other being in regeneration mode, the reactor functioning in regeneration mode being connected to a regeneration section comprising a feed/effluent exchanger, a cooling exchanger, a separator for condensing water of reaction, and a compressor for recirculating regeneration gas.

5. The process as claimed in claim 4, wherein, when one of the two reactors of said catalytic conversion unit (22) is in regeneration mode, regeneration is carried out by burning coke deposited on the catalyst, and said burning is performed by injecting a quantity of air, optionally diluted with an inert gas, which increases the temperature in said one of two reactors in regeneration mode up to a maximum of 50° C. higher.

6. The process as claimed in claim 1, wherein the effluents removed from the catalytic conversion unit (22) comprise a gas stream effluent (27) and, prior to being introduced into the catalytic conversion unit (22), the fuel gas (15) is combined with a recycled portion (38) of the gas stream effluent (27) to form a mixture, said mixture is pre-heated in a feed-effluent exchanger (221) and then sent to a reactor (223) of the catalytic conversion unit (22), converted effluent (228) discharged from the catalytic conversion unit (22) is cooled in said feed-effluent exchanger (221) and then further cooled by cooling water in a chiller (230) to form a cooled effluent (23), the cooled effluent (23) is separated in a separator (24) into a liquid phase (28) and a gas phase (25), said gas phase (25) is compressed by a compressor (26) and then sent to the first absorption section (31), and said liquid phase (28) is sent to the first absorption section (31) via a pump (29).

7. The process as claimed in claim 1, wherein the catalytic conversion unit (22) operates under the following operating conditions:
   temperature in the range of 500° C. to 650° C., and
   a partial pressure of ethylene in the range of 1 to 2 bar absolute.

8. The process as claimed in claim 3, wherein the portion (38) of the gas stream effluent (27) that is recycled to the catalytic conversion unit (22) is an amount equal to between 25% and 200% of the amount of the gas stream effluent (27) that is introduced into the first absorption section (31).

\* \* \* \* \*